United States Patent [19]

Schwindt et al.

[11] 4,276,386

[45] Jun. 30, 1981

[54] DIISOCYANATES HAVING UREA GROUPS, A PROCESS FOR THEIR PREPARATION AND THEIR USE IN THE PRODUCTION OF POLYURETHANES

[75] Inventors: Jürgen Schwindt; Gerhard Grögler, both of Leverkusen, Fed. Rep. of Germany

[73] Assignee: Bayer Aktiengesellschaft, Leverkusen, Fed. Rep. of Germany

[21] Appl. No.: 152,285

[22] Filed: May 22, 1980

[30] Foreign Application Priority Data

Jun. 6, 1979 [DE] Fed. Rep. of Germany ....... 2922966

[51] Int. Cl.$^3$ ..................... C08G 18/77; C08G 18/14
[52] U.S. Cl. ............................ 521/160; 260/453 AR; 521/162; 528/59; 528/67
[58] Field of Search ................... 528/59, 67; 521/160, 521/162; 260/453 AR

[56] References Cited

U.S. PATENT DOCUMENTS

| | | | |
|---|---|---|---|
| 2,597,025 | 5/1952 | Orth | 260/77.5 |
| 2,757,184 | 7/1956 | Pelley | 260/453 |
| 2,902,474 | 9/1959 | Arnold et al. | 260/77.5 |
| 3,361,844 | 1/1968 | Hoeschele | 528/67 |
| 3,454,606 | 7/1969 | Brotherton et al. | 260/453 AR |
| 3,906,019 | 9/1975 | Campbell et al. | 260/453 P |
| 3,943,158 | 3/1976 | Dietrich et al. | 528/67 |
| 4,055,548 | 10/1977 | Carleton et al. | 528/67 |

FOREIGN PATENT DOCUMENTS 2747072  4/1979  Fed. Rep. of Germany ... 260/453 AR

*Primary Examiner*—H. S. Cockeram
*Attorney, Agent, or Firm*—Gene Harsh; Joseph C. Gil

[57] ABSTRACT

This invention relates to new diisocyanates containing urea groups which are liquid at room temperature or can be liquefied by heating to a temperature of up to 80° C. These novel diisocyanates may be in the form of solutions in isocyanate prepolymers. The invention also is directed to a process for preparation of these new diisocyanates by the reaction of special diisocyanate starting materials and water and to their use as components for the production of polyurethanes.

17 Claims, No Drawings

DIISOCYANATES HAVING UREA GROUPS, A PROCESS FOR THEIR PREPARATION AND THEIR USE IN THE PRODUCTION OF POLYURETHANES

BACKGROUND OF THE INVENTION

This invention relates to new diisocyanates containing urea groups which are liquid at room temperature or can be liquefied by heating to a temperature of up to 80° C. These novel diisocyanates may be in the form of solutions in isocyanate prepolymers. The invention also is directed to a process for preparation of these new diisocyanates by the reaction of special diisocyanate starting materials and water and to their use as components for the production of polyurethanes.

It has long been known that the reaction of water with monoisocyanates leads to substituted ureas and the reaction of water with polyisocyanates leads to high molecular weight polyureas. Resinous polyureas containing isocyanate groups can be obtained according to U.S. Pat. No. 2,597,025 by using from 0.3 to 0.6 mol of $H_2O$ per mol of aromatic diisocyanate in suitable solvents. It has also been disclosed that aromatic diisocyanates can undergo a selective reaction with water to produce low molecular weight diisocyanate ureas. U.S. Pat. Nos. 2,757,184; 2,757,185; and 3,906,019 describe the reaction of 2,4-diisocyanatotoluene with water under suitable reaction conditions to yield the corresponding bis-(3-isocyanatotoly)-urea. The analogous reaction of 2,6-diisocyanatotoluene to produce 1,3-bis-(3-isocyanatotolyl)-urea has been disclosed (U.S. Pat. Nos. 3,906,019 and 2,902,474). All these processes are carried out in solvents. The diisocyanates must be readily soluble in the solvents and the water added must be at least partially soluble. The solvent must not exert any polymerizing action on the isocyanate and must be free from isocyanate-reactive functional groups.

The main disadvantage of known diisocyanates containing urea groups is that when produced by known processes, they invariably are obtained as solids of widely varying particle sizes which are infusible or can be melted only at very high temperatures. Thus, processing of such solids for use as starting materials in the production of polyurethanes, for example, requires their conversion into finely divided form by elaborate grinding processes after they have been first isolated by filtration and vacuum treatment to remove solvents adhering to them. Furthermore, due to the high melting point and low solubility of these known diisocyanates containing urea groups, products obtained from reactions in which they are used are not homogeneous and often have poor mechanical properties. Due to the solid state and low solubility of urea diisocyanates known in the art, it is difficult to observe accurate equivalent ratios of isocyanate groups to isocyanate-reactive groups when processing them, since the ureadiisocyanate particles often react only on the surface so that the reaction products from an envelope enclosing unreacted urea diisocyanate.

However, diisocyanates which contain urea groups are valuable starting materials for the production of polyurethanes since the urea segments incorporated in the end products often improve the mechanical properties of the polyurethanes.

Objects of the present invention are to provide new urea diisocyanates for the production of polyurethanes having improved mechanical properties, to overcome the disadvantages of the urea diisocyanates known in the art, and to provide a process for the preparation of these urea diisocyanates which does not have the disadvantages of processes known in the art.

These objects surprisingly can be achieved by reacting certain sulfur-containing diisocyanates with water to produce the corresponding diisocyanates containing urea groups.

DESCRIPTION OF THE INVENTION

The present invention relates to diisocyanates containing urea groups which are liquid at room temperature or which can be liquefied by heating to a temperature of not more than 80° C., corresponding to the formula:

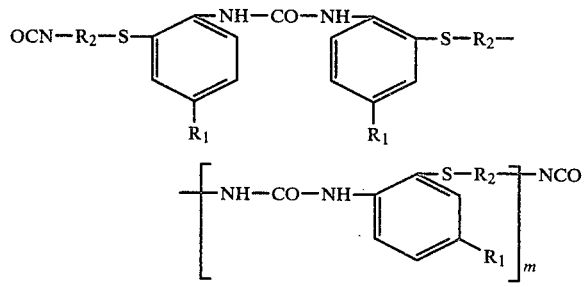

wherein m represents a whole or fractional number (on statistical average) of from 0 to 3, preferably 0;

$R_1$ represents hydrogen, an alkyl group having from 1 to 4 carbon atoms or an alkylthio group having from 1 to 4 carbon atoms; and $R_2$ represents a phenylene group optionally substituted by alkyl groups having from 1 to 4 carbon atoms or by an alkylthio group having from 1 to 4 carbon atoms, or it represents a linear or branched chain aliphatic hydrocarbon group having from 2 to 12 carbon atoms, at least 2 carbon atoms being situated between the nitrogen atom and the sulfur atom.

The invention also relates to mixtures which are liquid at room temperature or can be liquefied by heating to a temperature of not more than 80° C. comprising from 5 to 50% by weight of the diisocyanates containing urea groups and isocyanate prepolymers, which are liquid at room temperature or can be liquefied by heating to a temperature of not more than 80° C., the prepolymers corresponding to the formula:

wherein n represents a whole or fractional number (on statistical average) of from 2 to 4;

A represents a residue of the type obtained by the removal of the isocyanate groups from an organic diisocyanate; and D represents a residue of the type obtained by the removal of the hydroxyl groups from an n-functional polyhydroxyl compound having a molecular weight in the range of from 500 to 8,000 or by the removal of the hydroxyl groups from a mixture of such polyhydroxyl compounds.

It is preferred to use isocyanate prepolymers of the specified formula
wherein n represents 2; and A represents an aliphatic hydrocarbon group having from 6 to 12, preferably 6 carbon atoms, where at least 6 carbon atoms are situated between the 2 nitrogen atoms, a cycloaliphatic hydrocarbon group having from 4 to 15 carbon atoms, an aromatic hydrocarbon group having from 6 to 15 carbon atoms, a xylylene group or a group of the formula:

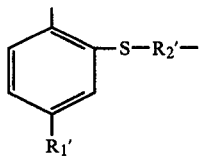

in which $R_1'$ represents hydrogen; and $R_2'$ represents a polymethylene group having from 2 to 6 carbon atoms or a 1,4-phenylene group.

The mixtures of the diisocyanates containing urea groups and the isocyanate prepolymers preferably are liquid solutions, pastes or solid solutions which can be liquefied by heating to not more than 80° C.

The present invention also relates to a process for the preparation of these new diisocyanates containing urea groups comprising reacting diisocyanates of the formula:

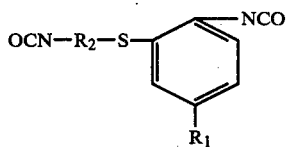

wherein $R_1$ and $R_2$ are as defined above with from 0.4 to 0.8 mol of water per mol of diisocyanate, or with a corresponding quantity of a compound from which water is split off. The resulting diisocyanate containing urea groups optionally is subsequently dissolved in from 50 to 95% by weight, based on the whole mixture, of an isocyanate prepolymer of the type defined above.

Additionally, the present invention relates to the use of these new diisocyanates, optionally dissolved in isocyanate prepolymers, as starting components for the production of polyurethanes by the isocyanate polyaddition process.

Preparation of the diisocyanates used as starting material for the process of the invention is carried out as described in German Patent Application No. P 29 16 135.1 by phosgenation of diamines of the formula:

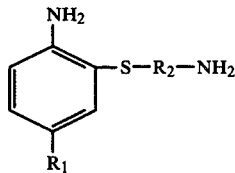

wherein $R_1$ and $R_2$ have the definitions above.

Diamines containing thioether groups which may be used as starting materials for the preparation of corresponding diisocyanates can be obtained by methods known in the art. Thioether group-containing amines having an aliphatically bound amino group, for example, may be obtained by a process analogous to that described in German Offenlegungsschrift No. 27 34 575 in which the corresponding sodium aminothiophenolates of the formula:

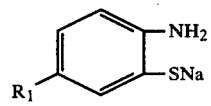

are reacted with the appropriate chloramines of the formula:

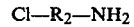

wherein $R_2$ is an aliphatic group. The above-mentioned sodium thiophenolates are readily obtained by alkaline saponification of the corresponding benzothiazoles.

Diamines containing exclusively aromatically bound amino groups and thioether groups may be obtained, for example, by the reaction of known o-amino substituted sodium-thiophenolates with the appropriate p-nitrochlorobenzenes of the formula:

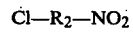

to produce intermediate compounds containing an amino group and a nitro group, followed by reduction of the nitro group to the amino group, for example, by means of zinc/hydrogen chloride or the use of Raney nickel as catalyst. The preparation of the intermediate compounds has been outlined, for example, in J. Chem. Soc. London, 1930, 180 et. seq.

Another example of a method for the preparation of thioethers containing two aromatically bound amino groups is the reaction of the last-mentioned p-nitrochlorobenzenes with sodium sulfide to form the corresponding p-aminothiophenolates of the formula:

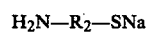

followed by their condensation with o-chloronitrobenzenes of the formula:

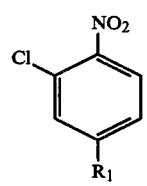

which is again followed by reduction to an amino group of the nitro group still present. Preparation of an intermediate stage containing an amino group and a nitro group carried out on this principle has been described, for example, in J. Chem. Soc. London, 1930, 180.

Finally, the diamines containing thioether groups and two aromatically bound amino groups may also be obtained by reaction of the corresponding o-nitrothiophenolates with the appropriate p-nitrochlorobenzenes or by reaction of the corresponding p-nitrothiophenolates with o-nitrochlorobenzenes to produce the intermediate stage containing two nitro groups, followed by reduction of the nitro groups of the intermediate stage to amino groups. The preparation of the intermediate compound obtained in this method has been described, for example, in Journal of the American Chemical Society 45, 1399 et. seq.

The following are examples of suitable diamines: 2-(2-aminoethylthio)-aniline; 2-(6-aminohexylthio)-aniline; 2-(12-aminododecylthio)-aniline; 2-(2-aminoethylthio)-5-methoxy aniline; 2-(2-aminoethylthio)-5-chloro aniline; 2-(6-aminohexylthio)-5-ethylsulfono aniline; 2,4'-diaminodiphenyl sulfide; and 2,4'-diamino-3'-ethylthiodiphenyl sulfide.

Phosgenation of the diamines exemplified above to the corresponding diisocyanates is carried out by known methods, preferably using a suitable auxiliary solvent such as chlorobenzene at a temperature of from −20° C. to 130° C. Suitable methods of phosgenation have been described, for example, in High Polymers XVI "Polyurethanes Chemistry and Technology", Part I, Interscience Publishers, New York, London 1962, pages 17 et seq.

The diisocyanates obtained by the phosgenation reaction naturally correspond in structure to the diamines used as starting materials.

The process of the invention may generally be carried out according to one of the following two embodiments.

In the first embodiment, the sulfur-containing starting diisocyanates are used in the process of the invention as solutions of from 10 to 90% by weight, preferably from 30 to 70% by weight, of sulfur-containing diisocyanates in an inert solvent and reacted at a temperature of from 25° to 100° C., preferably from 40° to 70° C., with from 0.4 to 0.8 mol, preferably from 0.5 to 0.6 mol, of water or a corresponding quantity of a compound releasing water, per mol of starting diisocyanate. The solution of starting diisocyanate is preferably introduced into the reaction vessel first and then the water of compound which splits off water is added to the solution. The progress of the reaction can easily be followed and controlled by determination of the volume carbon dioxide released. The solvent may be removed after the reaction, for example, by distillation. If the solvent is removed by distillation, the compounds of the invention are contained in the distillation residue. The following are examples of suitable inert solvents: acetone, methylethyl ketone, methyl isobutyl ketone, dioxane, cyclohexanone, ethylacetoacetate and acetyl acetone.

Examples of suitable compounds from which water can be split off include: formic acid, tertiary alcohols such as tertiary butanol and organic and inorganic compounds containing water of crystallization such as pinacol hexahydrate, chloral hydrate or sodium sulfate decahydrate. However, liquid water preferably is used rather than compound which split off water.

In a second embodiment, the starting diisocyanate containing sulfur is mixed with an isocyanate prepolymer of the previously specified formula:

which should be either liquid at room temperature or capable of being melted by heating to not more than 80° C. The sulfur-containing diisocyanate and the prepolymer are used in such proportions that the overall mixture contains from about 5 to 50% by weight, preferably from 5 to 25% by weight of the starting diisocyanate. Water or a water releasing compound is then added under vigorous mixing conditions to the resulting mixture in an amount corresponding to from 0.4 to 0.8 mol of water, preferably from 0.5 to 0.6 mol of water, for each gram-equivalent of isocyanate groups in the sulfur-containing diisocyanate. The reaction mixture is kept within the temperature range of from 25° to 100° C., preferably from 40° to 70° C. The progress of the reaction can be followed volumetrically from the quantity of carbon dioxide liberated. Solutions of the diisocyanates containing urea groups of the invention is the isocyanate prepolymer are directly obtained by this method.

Polyols of the formula:

wherein D has the same definition as above, used for the preparation of the isocyanate prepolymers may be polyesters, polyethers, polythioethers, polyacetals, polycarbonates or polyester amides having a molecular weight in the range of from 500 to 8,000, preferably from 1,000 to 3,000, and having from 2 to 4, preferably 2 hydroxyl groups, such as those known for the production of both noncellular and cellular polyurethanes. It is preferable to use the corresponding polyester polyols or polyether polyols.

Examples of suitable polyesters containing hydroxyl groups include the reaction products of polyhydric, preferably dihydric alcohols, optionally with the addition of trihydric alcohols, and polybasic, preferably dibasic carboxylic acids. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic and/or heterocyclic and they may be substituted, e.g., by halogen atoms, and/or unsaturated. Examples of suitable polycarboxylic compounds include: succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride; endomethylene tetrahydrophthalic acid anhydride; glutaric acid anhydride; maleic acid; maleic acid anhydride; fumaric acid; dimeric and trimeric fatty acids such as oleic acid optionally mixed with monomeric fatty acids; dimethyl terephthalate and terephthalic acid-bis-glycol esters. The following are examples of suitable polyhydric alcohols; ethylene glycol; propylene glycol-(1,2) and -(1,3); butylene glycol-(1,4) and -(2,3); hexanediol-(1,6); octanediol-(1,8); neopentylglycol; cyclohexanedimethanol (1,4-bis-hydroxymethylcyclohexane); 2-methyl-1,3-propanediol; glycerol; trimethylol propane; hexanetriol-(1,2,6); butanetriol-(1,2,4); trimethylolethane; diethylene glycol; triethylene glycol; tetraethylene glycol; polyethylene glycols; dipropylene glycol; polypropylene glycols; dibutylene glycol and polybutylene glycols. Polyesters of lactones such as ε-caprolactone or hydroxycarboxylic acids such as ω-hydroxycaproic acid may also be used.

The polyethers which may be used in the present invention which have from 2 to 4, preferably 2 hydroxyl groups are generally known and are prepared, for example, by self-polymerization of epoxides such as ethylene oxide, propylene oxide, butylene oxide, tetrahydrofuran, styrene oxide or epichlorohydrin, e.g., in the presence of $BF_3$. The polyethers also may be obtained by the addition of these epoxides, optionally as mixtures or successively, to starting components having reactive hydrogen atoms, such as water, alcohols or amines. Examples of suitable starting components include ethylene glycol, propylene glycol-(1,3) or -(1,2), trimethylolpropane, 4,4'-dihydroxydipheyl propane, aniline, ammonia, ethanolamine or ethylene diamine. It is often preferred to use polyethers which contain predominantly primary OH groups (i.e., up to 90% by weight based on all the OH groups present in the polyether). Polyethers modified with vinyl polymers, e.g., the compounds obtained by the polymerization of styrene and acrylonitrile in the presence of polyethers (U.S. Pat. Nos. 3,383,351; 3,304,273; 3,523,093; and 3,110,695 and German Pat. No. 1,152,536) are also suitable.

Examples of suitable polythioethers include the self-condensation products of thiodiglycol and/or the condensation products of thiodiglycol with other glycols, dicarboxylic acids, formaldehyde, aminocarboxylic acids or amino alcohols. The products obtained are polythio mixed ethers, polythio ether esters or polythio ether ester amides depending on the co-components.

Suitable polyacetals include, for example, the compounds which can be prepared from glycols such as diethylene glycol, triethylene glycol, 4,4'-dioxethoxydiphenyl dimethyl methane, hexanediol and fromaldehyde. Suitable polyacetals for the purpose of the present invention may also be prepared by the polymerization of cyclic acetals.

Suitable polycarbonates having hydroxyl groups which may be used are generally known. Examples include those polycarbonates which can be prepared by the reaction of diols such as propanediol-(1,3), butanediol-(1,4) and/or hexanediol;-(1,6), diethylene glycol, triethylene glycol or tetraethylene glycol with diarylcarbonates such as diphenylcarbonate, or with phosgene.

Polyhydroxyl compounds already containing urethane or urea groups and modified or unmodified natural polyols such as castor oil may be used.

Representatives of these compounds which may be used in the present invention have been described, for example, in High Polymers, Vol. XVI, "Polyurethanes, Chemistry and Technology" by Saunders Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Höchtlen, Carl-Hanser-Verlag, Munich, 1966, e.g., on pages 45 to 71. Mixtures of these compounds may also be used, such as mixtures of polyethers and polyesters.

The polyester diols and polyether diols corresponding to the above description are preferred.

Examples of suitable diisocyanates corresponding to the formula:

A(NCO)$_2$ wherein A represents a residue of the type obtained by the removal of the isocyanate groups from an organic diisocyanate for the preparation of the isocyanate prepolymers include: tetramethylene diisocyanate; hexamethylene diisocyanate; 1,12-dodecane diisocyanate; cyclobutane-1,3-diisocyanate; cyclohexane-1,3- and -1,4-diisocyanate and mixtures of these isomers; 1-isocyanato-3,3,5-trimethyl-5-isocyanatomethylcyclohexane; 2,4- and 2,6-hexahydrotolylene diisocyanate and mixtures of these isomers; hexahydro-1,3- and-/or -1,4-phenylene diisocyanate; perhydro-2,4'- and/or -4,4'-diphenylmethane diisocyanate; 1,3- and 1,4-phenylene diisocyanate; 2,4- and 2,6-tolylene diisocyanate and mixtures of these isomers; diphenyl methane-2,4'- and-/or -4,4'-diisocyanate; naphthylene-1,5-diisocyanate; 2,4'-diisocyanatodiphenyl sulfide; 2-(ω-isocyanatoalkylthio)-phenyl isocyanates; polyisocyanates having carbodiimide groups as described in German Pat. No. 1,092,007; and the diisocyanates described in U.S. Pat. No. 3,492,330. Mixtures of these diisocyanates may also be used.

Generally, it is particularly preferred to use diisocyanates such as 2,4- and 2,6-tolylene diisocyanate and any mixtures of these isomers ("TDI"), and 2,4'-and/or 4,4'-diisocyanatodiphenyl methane.

According to a preferred variation of the second embodiment of the process of the invention, the isocyanate prepolymers are prepared in situ by reaction of the polyols of the type exemplified with an excess of the sulfur-containing diisocyanate used as a starting material. The sulfur-containing diisocyanate is used in such an excess over the quantity required for NCO/OH equivalent ratio of 2:1 that solutions of excess sulfur-containing diisocyanate in the developing isocyanate prepolymer containing from about 5 to 50% by weight, preferably from 5 to 25% by weight, of the free, starting sulfur-containing diisocyanate are obtained directly. In this preferred variation, the group A in the formula for the isocyanate prepolymer corresponds, of course, to the group obtained by removal of the isocyanate groups from the sulfur-containing diisocyanate of the specified formula used as starting material. The water or water-releasing compound may then be addd as in the second embodiment previously described.

The urea diisocyanates of the present invention are either liquids at room temperature or in many cases, substances which are pasty at room temperature, but which can be liquefied by simply heating to a temperature of not more than 80° C. The physical states of the compounds of the invention depend mainly on the value of the index m for the urea diisocyanate. The particularly preferred urea diisocyanates of the present invention in which m=O are generally liquid at room temperature. The value for m depends on the molar ratio of isocyanate/water used in the process of the invention. Such compounds in which m=O are obtained in a substantially selective reaction when 0.5 mol of water is used per gram-equivalent of isocyanate groups in the diisocyanates used as a starting material in the process of the invention. This selectivity of the reaction is due to the selective reactivity of the isocyanate groups in the starting diisocyanates. If water is not used in excess, the aromatic isocyanate group in the ortho position to the sulfur atom is generally the first to react.

Since isocyanate prepolymers which are liquid at room temperature or which can be melted by heating to 80° C. are used in the second embodiment of the process of the invention, solutions of the urea diisocyanates in these isocyanate prepolymers are also liquid at room temperature or can be liquefied by simply heating to not more than 80° C. Such systems can, of course, also be obtained by mixing appropriate quantities of separately prepared urea diisocyanates of the invention with the isocyanate prepolymers.

The quantity of free, unreacted sulfur-containing diisocyanate present in the compounds of the present invention or their solutions in isocyanate prepolymers is generally less than 0.6% by weight if at least 0.5 mol of water is used per gram-equivalent of isocyanate groups of the sulfur-containing diisocyanates used as starting material.

It would be possible in principle, although it is less preferred, to use isocyanate prepolymers which melt above 80° C. for the process of the invention. In that case, it is advisable to use compounds which split off water, such as pinacol, hexahydrate, instead of water itself, and to add inactivating acidic compounds such as phosphoric acid, toluene sulfonic acid or benzyl chloride in a quantity of from 0.01 to 0.1% by weight based on the reaction mixture to prevent side reactions such as biuret formation. These compounds are also necessary when tertiary butanol is used as a source of water, to reduce the decomposition temperature of the tertiary butyl urethane originally formed. Solutions of urea diisocyanates of the present invention which can be melted by heating to a temperature of not more than 80° C. are, in many cases, also obtained when the isocyanate prepolymers melt at a temperature above 80° C.

Compounds known in the literature to accelerate diisocyanate addition reactions, such as tertiary amines or organometallic compounds, are generally avoided when carrying out the process of the present invention, in order to prevent the formation of high molecular weight polyureas which contain substantially no isocyanate groups.

The urea diisocyanates of the invention are particularly valuable starting materials for the preparation of polyurethanes. Polyurethane elastomers produced from them have particularly interesting mechanical properties due to the urea segments contained in them. At the same time, due to their liquid consistency at a temperature below 80° C., the compounds of the present invention may be handled easily. Yet, they are physiologically harmless due to their low vapor pressure.

The urea diisocyanates of the invention and their solutions in the isocyanate prepolymers are particularly suitable for the production of polyurethane elastomers.

When the urea diisocyanates of the invention are used in the production of polyurethane elastomers, the solutions of the new compounds in isocyanate prepolymers, for example, may be reacted by a known method with known chain lengthening agents. The equivalent ratio of isocyanate groups to isocyanate-reactive groups in the chain lengthening agents is generally in the range of from 0.9:1 to 1.2:1, most preferably from 1:1 to 1.1:1.

The chain lengthening agents used may be, for example, water, simple glycols having a molecular weight of from 62 to 500 or organic diamines containing two primary and/or secondary amino groups having a molecular weight of from 62 to 500. Hydrazines may also be used as chain lengthening agents. Examples of suitable organic diamines include: aliphatic diamines such as ethylene diamine and hexamethylene diamine; and cycloaliphatic diamines such as 4,4'-diaminodicyclohexyl methane or 1-methyl-2,4-diaminocyclohexane. Aromatic diamines are preferred and include such diamines as: bis-anthranilic acid esters according to German Offenlegungsschrifts Nos. 2,040,644 and 2,160,590; 3,5- and 2,4- diamino-benzoic acid esters according to German Offenlegungsschrift No. 2,026,900; the diamines having ester groups described in German Offenlegungsschrifts Nos. 1,803,635; 2,040,650; and 2,160,589; 3,3'-dichloro-4,4'-diaminodiphenyl methane; 3,3'-dithioether-4,4'-diaminodiphenyl methane; phenylene diamines; tolylene diamines; 3,5-diethyl-2,4-diaminotoluene; 4,4'-diaminodiphenyl methane; 2,2'-diaminodiphenyl sulfide; 2,4'-diaminodiphenyl sulfide and 4,4'-diaminodiphenyl sulfide.

Examples of suitable glycols which may be used as chain lengthening agents include: ethylene glycol; propylene glycol-(1,2) and -(1,3); butanediol-(1,4) and -(2,3); pentanediol-(1,5); hexanediol-(1,6); octanediol-(1,8); neopentyl glycol; 1,4-bis-hydroxy methyl cyclohexane; 2-methyl-1,3-propanediol; butenediol; butynediol; monochlorohydrin; glycerol-monoalkyl- or -mono-aryl ethers; xylylene glycols; and the Diels-Alder addition product of butenediol and anthracene or hexahydropyrocatechol.

When the chain lengthening agents are reacted with the urea diisocyanates of the invention or their solutions in isocyanate prepolymers, all the free isocyanate groups react smoothly whereas when solid urea diisocyanates or their suspensions are used, the reaction depends to a great extent on the particle size of the urea diisocyanates and the solubility of the reaction products of the solid urea diisocyanates with the diol or diamine in the isocyanate prepolymer. Even minute particles of urea diisocyanates behave as fillers in that the polyurethane or polyurea formed on the surfaces of the particles by the reaction with chain lengthening agents encapsulates unreacted urea diisocyanate. This behavior as fillers is a serious disadvantage in polyurethane production since it greatly reduces the mechanical and dynamic properties of the polyurethanes and forms weak zones in the polyurethanes which tend to cause breaking under loads at these zones. The relatively high molecular weight polyhydroxyl compounds mentioned as examples for the production of the isocyanate prepolymers may, of course, also be included when the new urea diisocyanates are used for the production of polyurethanes.

When the new diisocyanates of the present invention are used for the production of polyurethanes, in particular polyurethane elastomers, known auxiliary agents and additives such as plasticizers, dyes and fillers may also be added. Phthalic acid esters and organic sulfonamides, for example, are suitable plasticizers. It is often particularly advantageous to use plasticizers which contain sulfur, such as methylene-bis-thioglycolic acid butylester.

Fillers and pigments such as titanium dioxide, silicon dioxide, bentonite, calcium silicate and carbon black may also be used. They may be direcly incorporated in the higher molecular weight polyhydroxyl compound or in the isocyanate prepolymer.

The polyurethane elastomers produced using the process of the invention have excellent mechanical properties, improved high temperature characteristics and excellent resistance to organic solvents and oils. This enables them to be used in a wide variety of fields, for example, as roller cloths, elastic parts for machines, seals, buffers, bellows, linings for ball mills, shoe soles, gear wheels and automobile tires.

The following examples illustrate the invention. All quantities are in parts by weight or percentages by weight unless otherwise indicated. Examples 1(a) through 1(i) illustrate the preparation of liquid urea diisocyanates containing sulfur.

EXAMPLE 1(a)

1.8 g of water in 50 ml of anhydrous acetone are added dropwise within 15 minutes to 53.6 g (0.2 mol) of 2,4'-diisocyanatodiphenyl sulfide in 200 ml of anhydrous acetone at 50° to 55° C. Evolution of gas begins instantly. The mixture is stirred at 50° to 55° C. until no more gas evolves. Acetone is removed under vacuum. A liquid which is highly viscous at room temperature and has the chemical composition corresponding to the following formula is left behind:

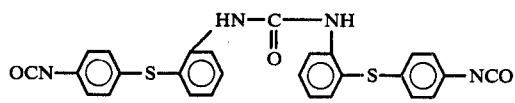

Isocyanate content (calculated) 16.5%.
Isocyanate content (found) 16.25%.

The following liquid urea diisocyanates containing sulfur are synthesized by methods analogous to that of Example 1(a) (see Table).

(OH number =56) and 2,4-tolylene diisocyanate (NCO:OH =2:1) is mixed at a temperature of from 60° to 70° C. with 15% of the urea diisocyanate of Example 1(a). The solution of urea diisocyanate in the prepolymer has an isocyanate content of 5.4%.

EXAMPLE 3

85% of an isocyanate prepolymer containing 3.4% NCO and prepared from a polypropylene glycol ether having a molecular weight of 2,000 (OH number =56) and a commercial diisocyanatodipenyl methane mixture having an NCO content of 33.3% (NCO:OH =2:1) is mixed at from 60° to 70° C. with 15% of the urea diisocyanate of Example 1(b) mentioned in the Table. The solution has an isocyanate content of 5%.

| Diisocyanate | Urea Diisocyanate | % Isocyanate content (Calc.) | (Found) |
|---|---|---|---|
| (b) 2,4′-diisocyanato-3′-ethyl-diphenyl sulfide | [structure] | 14.8 | 14.65 |
| (c) 2,4′-diisocyanato-3′-ethyl thio-diphenyl sulfide | [structure] | 13.3 | 13.35 |
| (d) 2,4′-diisocyanato-5-ethyl-diphenyl sulfide | [structure] | 14.8 | 14.7 |
| (e) 2,4′-diisocyanato-5-isopropyl thio-diphenyl sulfide | [structure] | 12.8 | 12.6 |
| (f) 2-(2-isocyanatoethyl-thio)-phenyl isocyanate | [structure] | 20.3 | 20.15 |
| (g) 2-(6-isocyanato-hexylthio)-phenyl isocyanate | [structure] | 16.5 | 16.3 |
| (h) 2-(2-isocyanato-ethylthio)-4-ethyl phenyl isocyanate | [structure] | 17.9 | 17.75 |
| (i) 2-(6-isocyanato hexylthio)-4-isopropylthio-phenyl isocyanate | [structure] | 12.45 | 12.55 |

Examples 2 through 20 illustrate solutions of sulfur-containing liquid urea diisocyanates in isocyanate prepolymers.

EXAMPLE 2

85% of an isocyanate prepolymer having an isocyanate content of 3.5%, prepared from a linear polypropylene glycol ether having a molecular weight of 2,000

EXAMPLE 4

90% of an isocyanate prepolymer having an isocyanate content of 3.5% and prepared from 2,4-tolylene diisocyanate and a linear polyester diol having a molecular weight of 2,000 (OH number =56) based on adipic acid and diethylene glycol is mixed at from 60° to 70° C. with 10% of the urea diisocyanate of Example 1(f) mentioned in the Table. The solution has an isocyanate content of 5.15%.

EXAMPLE 5

90% of the isocyanate prepolymer described in Example 4 is mixed at from 60° to 70° C. with 10% of the liquid urea diisocyanate of Example 1(g) shown in the Table. The isocyanate content of the solution is 4.8%.

EXAMPLE 6

85% of the isocyanate prepolymer described in Example 4 is mixed at from 60° to 70° C. with 15% of the liquid urea diisocyanate of Example 1(i) shown in the Table. The isocyanate content of the solution is 4.85%.

EXAMPLE 7

90% of the isocyanate prepolymer described in Example 2 is mixed at from 60° to 70° C. with 10% of the liquid urea diisocyanate of Example 1(d) shown in the Table. The isocyanate content of the solution is 4.6%.

EXAMPLE 8

90% of the isocyanate prepolymer described in Example 3 is mixed at from 60° to 70° C. with 10% of the liquid urea diisocyanate of Example 1(c) shown in the Table. The isocyanate content of the solution is 4.4%.

EXAMPLE 9

95% of an isocyanate prepolymer having an isocyanate content of 4.9% and prepared from a polyether polyol mixture of 45% of a linear polypropylene glycol having a molecular weight of 2,000, 5% of a trifunctional polypropylene glycol having a molecular weight of 4,800 and 50% of a linear polypropylene glycol having a molecular weight of 1,000 (OH number =112) and 2,4- tolylene diisocyanate (NCO/OH =2:1) is mixed with 5% of the liquid urea diisocyanate of Example 1(h) shown in the Table. The isocyanate content of the solution is 5.5%.

EXAMPLE 10

90% of the prepolymer described in Example 9 is mixed at from 60° to 70° C. with 10% of the liquid urea diisocyanate of Example 1(e) shown in the Table. The isocyanate content of the solution is 5.6%.

EXAMPLE 11

85% of an isocyanate prepolymer having an isocyanate content of 3.3% and prepared from the polypropylene glycol ether diol of Example 2 and 2,4'-diisocyanatodiphenyl sulfide (NCO/OH =2:1) is mixed at from 60° to 70° C. with 15% of the liquid urea diisocyanate prepared according to Example 1(a). The isocyanate content of the solution is 5.25%.

EXAMPLE 12

268 g (1 mol) of 2,4'-diisocyanatodiphenyl sulfide are added to 2,348 g (1 mol) of an isocyanate prepolymer which has an isocyanate content of 3.5% and has been prepared from 2,000 g of a linear polypropylene glycol ether having a molecular weight of 2,000 (OH number =56) and 348 g (2.0 mol) of 2,4-diisocyanatotoluene. 9 g (0.5 mol) of water are added to this mixture at a temperature of from 50° to 60° C. within half an hour and the whole reaction mixture is maintained at this temperature for from 5 to 6 hours. When evolution of $CO_2$ has terminated (11.5 liters), a polyisocyanate-urea solution having a total isocyanate content of 4.7% is obtained.

EXAMPLE 13

The mixture of prepolymer and diisocyanate from Example 12 is mixed with 18.8 g of pinacol hexahydrate and reacted at from 60° to 70° C. (corresponding to 0.5 mol of water per mol of free 2,4'-diisocyanatodiphenyl sulfide). A polyisocyanate urea solution having a total isocyanate content of 4.5% is obtained after 5 to 6 hours at from 60° to 70° C.

EXAMPLE 14

296 g (1 mol) of 2,4'-diisocyanato-3'-ethyldiphenyl sulfide are added to 2,500 g (1 mol) of an isocyanate prepolymer having an isocyanate content of 3.4% which has been prepared from 2,000 g of a linear polypropylene glycol ether having a molecular weight of 2,000 and 500 g of a commercial mixture of diisocyanatodiphenyl methanes with an NCO-content of 33.3% by weight. 9 g (0.5 mol) of water are added to the resulting mixture within half an hour at from 50° to 60° C. and the mixture is stirred for from 5 to 6 hours. A polyisocyanate-urea solution having a total isocyanate content of 4.5% is obtained when evolution of $CO_2$ (11.3 liters) has terminated.

EXAMPLE 15

(a) 268 g (1 mol) of 2,4'-diisocyanatodiphenyl sulfide are added to 2,536 g (1 mol) of a prepolymer which has an isocyanate content of 3.3% and has been prepared from a polypropylene glycol polyether having a molecular weight of 2,000 and 536 g of 2,4'-diisocyanatodiphenyl sulfide. 9 g (0.5 mol) of water are added to the mixture at from 50° to 60° C. within half an hour and the mixture is stirred for from 5 to 6 hours. When evolution of $CO_2$ has terminated, a polyisocyanate urea solution having a total isocyanate content of 4.42% is obtained.

(b) 200 g of the polyether diol used in (a) are prepolymerized with 804 g of 2,4'-diisocyanatodiphenyl sulfide and then reacted with 9 g of water analogously to method (a). A polyisocyanate-urea solution having a total isocyanate content of 4.35% is obtained.

EXAMPLE 16

220 g (1 mol) of 2-(2-isocyanatoethylthio)-phenyl isocyanate are added to 2,336 g (1 mol) of a prepolymer having an isocyanate content of 3.6% prepared from a polyester diol having a molecular weight of 2,000 (OH number =56) of adipic acid and diethylene glycol and 336 g of 1,6-hexamethylene diisocyanate. 9 g of water are added to the mixture at from 50° to 60° C. within 0.5 hours and the mixture is stirred for from 6 to 7 hours. The total isocyanate content of the solution after termination of the reaction is 4.85%.

EXAMPLE 17

200 g of the polyester diol used in Example 16 are prepolymerized with 105 g of 2-(6-isocyanatohexylthio)-4-isopropylthio-phenyl isocyanate. 0.9 g of water are added at from 50° to 60° C. and the mixture is stirred for from 6 to 7 hours. The total isocyanate content of the solution after termination of the reaction is 4%.

EXAMPLE 18

26.8 g (0.1 mol) of 2,4'-diisocyanatodiphenyl sulfide are added to 253.6 g (0.1 mol) of the prepolymer from Example 15 (a). 1.1 g of water (0.61 mol) are slowly added dropwise at from 50° to 60° C. and the mixture is stirred for from 5 to 6 hours. The total isocyanate content is 4.15%.

EXAMPLE 19

22.0 g (0.1 mol) of 2-(2-isocyanatoethylthio)-phenyl isocyanate are added to 255.2 g (0.1 mol) of a prepolymer having an isocyanate content of 3.2% obtained from a polyester diol having a molecular weight of 2,000 and an OH number of 56 and 55.2 g (0.2 mol) of 2-(6-isocyanatohexylthio)-phenyl isocyanate. 1.3 g (0.72 mol) of water are slowly added dropwise at from 50° to 60° C. and the mixture is stirred for from 5 to 6 hours. The total isocyanate content is 3.7%.

EXAMPLE 20

(a) 33 g (0.15 mol) of 2-(2-isocyanatoethylthio)-phenyl isocyanate are added to 244.0 g (0.1 mol) of a prepolymer having an isocyanate content of 3.4% obtained from a polyester diol having a molecular weight of 2,000 and an OH number of 56 and 44.0 g (0.2 mol) of 2-(2-isocyanatoethylthio)-phenyl isocyanate. 1.8 g of water (0.1 mol) are added dropwise at from 50° to 60° C. for 45 minutes and the mixture is stirred for from 6 to 7 hours. The total isocyanate content is 4.5%.

(b) 200.0 g of the polyester diol used in (a) are mixed and prepolymerized with 77 g of 2-(2-isocyanatoethylthio)-phenyl isocyanate. The isocyanate content of the prepolymer is 10.6%. 1.8 g (0.1 mol) of water are added at from 50° to 60° C. as described in (a). The total isocyanate content is 4.4%.

Examples 21 through 27 illustrate the preparation of elastomers.

EXAMPLE 21

(a) 100 g of the polyisocyanate-urea solution having an isocyanate content of 5.4% prepared in Example 2 are degassed under vacuum at from 60° to 80° C. and stirred with 14.17 g of 4-chloro-3,5-diamino-benzoic acid-isobutylester within 30 seconds (NCO:NH$_2$ = 1.1:1). The reaction mixture is then poured into a metal mold which has been heated to a temperature of 120° C. The casting time is about 5 minutes. The molding can be removed after about 12 minutes.

(b) Analogous to (a) except that 10.4 g of 3,5-diethyl-2,4-diaminotoluene was used instead of the 4-chloro-3,5-diamino-benzoic acid-isobutylester.

The mechanical properties of the elastomers were determined in each case after tempering for 24 hours at 120° C.

|  | a | b |
|---|---|---|
| Tensile strength (DIN 53504) | 34.3 MPa | 32.1 MPa |
| Elongation at break (DIN 53504) | 644% | 670% |
| Tear propagation resistance (DIN 53515) | 35.7 KN/m | 35 KN/m |
| Shore hardness A (DIN 53505) | 85 | 83 |
| Elasticity (DIN 53512) | 55% | 53% |

EXAMPLE 22

100 g of the polyisocyanate-urea solution prepared in Example 4 are degassed under vacuum at from 80° to 100° C. and then stirred with 13.5 g of 3,5-diamino-4-chloro-benzoic acid isobutylester for 30 seconds. The NCO/NH$_2$ molar ratio is 1.1:1. The reaction mixture is poured into a mold which has been heated to 100° C. After a casting time of 3.5 minutes and a tempering time of about 10 hours at from 120° to 130° C., the molded body produced has the properties indicated below.

| Shore hardness A (DIN 53505) | 75.0 |
|---|---|
| Tensile strength (MPa) | 20.5 |
| Tear propagation resistance (KN/m) | 31.9 |
| Elasticity (%) | 48 |

EXAMPLE 23

(a) 100 g of the polyisocyanate-urea solution having an isocyanate content of 5.6% of Example 10 are degassed at 80° C. and then stirred with 10.8 g of 3,5-diethyl-2,4-diaminotoluene. After a casting time of 1 minute an elastic molded body is obtained which, when heated for a further 24 hours at 120° C., is found to have the mechanical properties set forth in the Table.

(b) Analogous to (a) except that 14.4 g of 4-chloro-3,5-diamino-benzoic acid isobutylester is used instead of the 3,5-diethyl-2,4-diaminotoluene.

|  | a | b |
|---|---|---|
| Tensile strength (MPa) | 38.5 | 37.6 |
| Elongation at break (%) | 480 | 510 |
| Tear propagation resistance (KN/m) | 43.3 | 46.8 |
| Shore hardness A | 88 | 90 |
| Elasticity (%) | 51 | 52 |

EXAMPLE 24

100 g of the polyisocyanate-urea solution prepared in Example 13 are degassed at 80° C. and stirred with 11.8 g of 4-chloro-3,5-diamino-benzoic acid isobutylester for 30 seconds (NCO-NH$_2$ = 1.1:1). The reaction mixture is poured into a mold which has been preheated to 100° C. The casting time is 5 minutes. The molding can be removed from the mold after 15 minutes. After a tempering time of 24 hours at 110° C., the elastomer obtained is found to have the following mechanical properties:

| Tensile strength (DIN 53504) | 17.5 MPa |
|---|---|
| Elongation at break (DIN 53504) | 638% |
| Tear propagation resistance (DIN 53515) | 24.2 KN/m |
| Shore hardness A (DIN 53505) | 78 |
| Elasticity (DIN 53512) | 50% |

EXAMPLE 25

100 g of the polyisocyanate-urea solution prepared in Example 14 are reacted with 11.8 g of 4-chloro-3,5-diamino-benzoic acid isobutylester as described in Example 24. The casting time is 4.5 minutes and the time before removal from the mold is 16 minutes. The mechanical properties of the elastomer are as follows:

| Tensile strength (DIN 53504) | 19.7 MPa |
|---|---|
| Elongation at break (DIN 52504) | 620% |
| Tear propagation resistance (DIN 53515) | 28.2 KN/m |
| Shore A (DIN 53505) | 85 |
| Elasticity (DIN 53512) | 51% |

EXAMPLE 26

100 g of the polyisocyanate-urea solution having an isocyanate content of 4.42% prepared in Example 15 (a) are mixed within 30 seconds at 100° C. with 11.6 g of 4-chloro-3,5-diamino-benzoic acid isobutylester (NCO:NH$_2$=1.1:1) and the mixture is poured into a mold which has been preheated to 110° C. The mixture remains in a pourable state for 4 minutes. The casting can be removed from the mold after 13 minutes. The following mechanical properties are obtained after a tempering time of 24 hours at 110° C.

| | |
|---|---|
| Tensile strength (DIN 53504) | 19.3 MPa |
| Elongation at break (DIN 53504) | 625% |
| Tear propagation resistance (DIN 53515) | 28.5 KN/m |
| Shore A (DIN 53505) | 77 |
| Elasticity (DIN 53512) | 49% |

EXAMPLE 27

100 g of the polyisocyanate-urea solutions prepared in Examples 20 (a) and 20 (b) and having isocyanate contents of 4.5 and 4.4%, respectively, are reacted at 100° C. with 11.8 g and 11.55 g, respectively, of 4-chloro-3,5-diamino-benzoic acid isobutylester as described in Example 26. (NCO/NH$_2$=1.1:1). The casting time is 6 minutes and the time until removal from the mold is 16 minutes. The mechanical properties of the two elastomers are as follows:

| | Solution 20 a | Solution 20 b |
|---|---|---|
| Tensile strength (DIN 53504) | 14.7 MPa | 14.8 MPa |
| Elongation at break (DIN 53504) | 825% | 850% |
| Tear propagation resistance (DIN 53515) | 21.4 KN/m | 22.4 KN/m |
| Shore A (DIN 53505) | 72 | 73 |
| Elasticity (DIN 53512) | 52% | 50% |

What is claimed is:

1. A diisocyanate containing urea groups, which is liquid at room temperature or can be liquefied by heating to a temperature of not more than 80° C., corresponding to the formula:

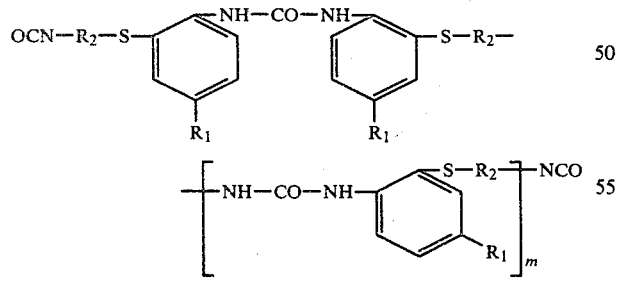

wherein
m represents a number of from 0 to 3 which may be whole or fractional (on statistical average),
R$_1$ represents hydrogen, an alkyl group having from 1 to 4 carbon atoms or an alkylthio group having from 1 to 4 carbon atoms, and
R$_2$ represents a phenylene group, optionally substituted by alkyl groups having from 1 to 4 carbon atoms or by an alkythio group having from 1 to 4 carbon atoms, or represents a linear or branched chain aliphatic hydrocarbon group having from 2 to 12 carbon atoms, with at least 2 carbon atoms being situated between the nitrogen atom and the sulfur atom.

2. A diisocyanate as claimed in claim 1 wherein m is zero.

3. A diisocyanate as claimed in claim 2 which is liquid at room temperature.

4. A mixture which is liquid at room temperature or can be liquefied by heating to a temperature of not more than 80° C. comprising:
(A) 5 to 50% by weight based on the mixture of a diisocyanate containing urea groups, which is liquid at room temperature or can be liquefied by heating to a temperature of not more than 80° C., corresponding to the formula:

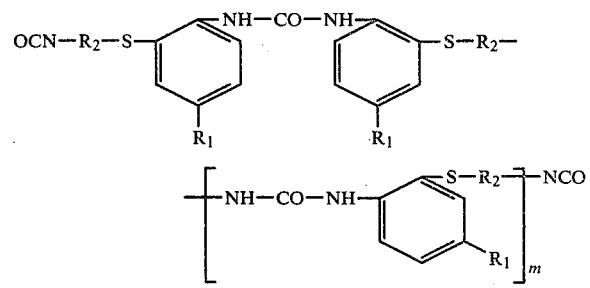

wherein
m represents a number of from 0 to 3 which may be whole or fractional (on statistical average),
R$_1$ represents hydrogen, an alkyl group having from 1 to 4 carbon atoms or an alkylthio group having from 1 to 4 carbon atoms, and
R$_2$ represents a phenylene group, optionally substituted by alkyl groups having from 1 to 4 carbon atoms or by an alkylthio group having from 1 to 4 carbon atoms, or represents a linear or branched chain aliphatic hydrocarbon group having from 2 to 12 carbon atoms, with at least 2 carbon atoms being situated between the nitrogen atoms and the sulfur atom; and
(B) an isocyanate prepolymer, which is liquid at room temperature or which can be liquefied by heating to a temperature of not more than 80° C., corresponding to the formula:

D$+$OCO—NH—A—NCO)$_n$ wherein
n has the value of a whole or fractional number, on statistical average, of from 2 to 4,
A represents a residue as is obtained by the removal of the isocyanate groups from an organic diisocyanate, and
D represents a residue of the type obtained by the removal of the hydroxyl groups from an n-functional polyhydroxyl compound within the molecular weight range of from 500 to 8,000 or by removal of the hydroxyl groups from a mixture of such polyhydroxyl compounds.

5. A mixture as claimed in claim 4 wherein said diisocyanate is in the form of a solution in said prepolymer.

6. A mixture as claimed in claim 4 wherein m represents zero, n represents 2, and A represents an aliphatic hydrocarbon group having from 6 to 12 carbon atoms with at least 6 carbon atoms situated between the 2 nitrogen atoms, a cycloaliphatic hydrocarbon group having from 4 to 15 carbon atoms, a xylylene group or a group corresponding to the formula:

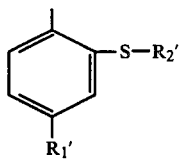

wherein $R_1'$ represents hydrogen, and $R_2'$ represents a polymethylene group having from 2 to 6 carbon atoms or a 1,4-phenylene group.

7. A mixture as claimed in claim 6, wherein said diisocyanate is in the form of a solution in said prepolymer.

8. A process for the preparation of a diisocyanate containing urea groups which is liquid at room temperature or can be liquefied by heating to a temperature of not more than 80° C. comprising reacting:

(A) a diisocyanate corresponding to the formula:

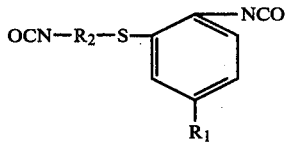

wherein $R_1$ represents hydrogen, an alkyl group having from 1 to 4 carbon atoms or an alkylthio group having from 1 to 4 carbon atoms, and $R_2$ represents a phenylene group, optionally substituted by alkyl groups having from 1 to 4 carbon atoms or by an alkylthio group having from 1 to 4 carbon atoms, or represents a linear or branched chain aliphatic hydrocarbon group having from 2 to 12 carbon atoms, with at least 2 carbon atoms being situated between the nitrogen atom and the sulfur atom; with (B) from 0.4 to 0.8 mol of water per mol of said diisocyanate or with a corresponding quantity of a compound which splits off water.

9. A process for the preparation of a mixture of a diisocyanate containing urea groups in an isocyanate prepolymer said mixture being a liquid at room temperature or liquefiable by heating to a temperature of not more than 80° C. comprising reacting:

(A) a diisocyanate corresponding to the formula:

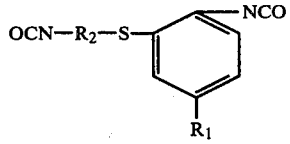

wherein $R_1$ represents hydrogen, an alkyl group having from 1 to 4 carbon atoms or an alkylthio group having from 1 to 4 carbon atoms, and $R_2$ represents a phenylene group, optionally substituted by alkyl groups having from 1 to 4 carbon atoms or by an alkylthio group having from 1 to 4 carbon atoms, or represents a linear or branched chain aliphatic hydrocarbon group having from 2 to 12 carbon atoms, with at least 2 carbon atoms being situated between the nitrogen atom and the sulfur atom; with (B) from 0.4 to 0.8 mol of water per mol of said diisocyanate or with a corresponding quantity of a compound which splits off water; and (C) from 50 to 95% by weight, based on the total mixture, of an isocyanate prepolymer which is liquid at room temperature or which can be liquefied by heating to a temperature of not more than 80° C., corresponding to the formula:

$$D\text{-}(OCO\text{---}NH\text{---}A\text{---}NCO)_n$$

wherein n has the value of a whole or fractional number, on statistical average, of from 2 to 4, A represents a residue as is obtained by the removal of the isocyanate groups from an organic diisocyanate, and D represents a residue of the type obtained by the removal of the hydroxyl groups from an n-functional polyhydroxyl compound within the molecular weight range of from 500 to 8,000 or by removal of the hydroxyl groups from a mixture of such polyhydroxyl compounds.

10. A process as claimed in claim 9 wherein n represents 2 and

A represents an aliphatic hydrocarbon group having from 6 to 12 carbon atoms with at least 6 carbon atoms situated between the 2 nitrogen atoms, a cycloaliphatic hydrocarbon group having from 4 to 15 carbon atoms, a xylylene group or a group corresponding to the formula:

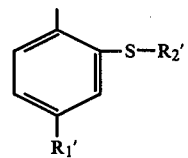

wherein $R_1'$ represents hydrogen and $R_2'$ represents a polymethylene group having from 2 to 6 carbon atoms or a 1,4-phenylene group.

11. A process as claimed in claim 9 wherein components (A) and (B) are first reacted and then added to component (C).

12. A process as claimed in claim 9 wherein components (A) and (C) are first added together and then reacted with component (B).

13. A process as claimed in claim 11 wherein n represents 2 and

A represents an aliphatic hydrocarbon group having from 6 to 12 carbon atoms with at least 6 carbon atoms situated between the 2 nitrogen atoms, a cycloaliphatic hydrocarbon group having from 4 to 15 carbon atoms, a xylylene group or a group corresponding to the formula:

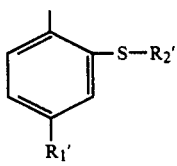

wherein
R₁' represents hydrogen and
R₂' represents a polymethylene group having from 2 to 6 carbon atoms or a 1,4-phenylene group.

14. A process as claimed in claim 12 wherein
n represents 2 and
A represents an aliphatic hydrocarbon group having from 6 to 12 carbon atoms with at least 6 carbon atoms situated between the 2 nitrogen atoms, a cycloaliphatic hydrocarbon group having from 4 to 15 carbon atoms, a xylylene group or a group corresponding to the formula:

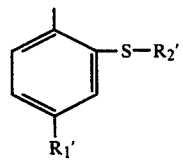

wherein
R₁' represents hydrogen and
R₂' represents a polymethylene group having from 2 to 6 carbon atoms or a 1,4-phenylene group.

15. A process for the preparation of polyurethanes comprising reacting an organic isocyanate with a compound containing isocyanate-reactive hydrogen atoms wherein said organic isocyanate comprises a diisocyanate containing urea groups, which is liquid at room temperature or can be liquefied by heating to a temperature of not more than 80° C. corresponding to the formula:

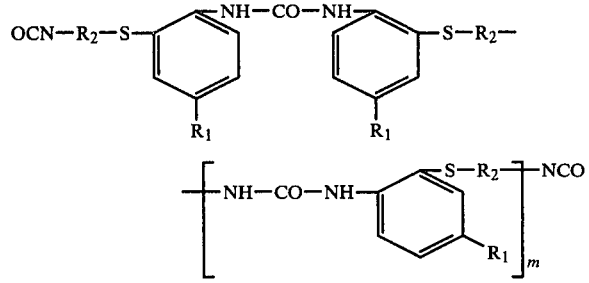

wherein
m represents a number of from 0 to 3 which may be whole or fractional (on statistical average),
R₁ represents hydrogen, an alkyl group having from 1 to 4 carbon atoms or an alkylthio group having from 1 to 4 carbon atoms, and
R₂ represents a phenylene group, optionally substituted by alkyl groups having from 1 to 4 carbon atoms or by an alkylthio group having from 1 to 4 carbon atoms, or represents a linear or branched chain aliphatic hydrocarbon group having from 2 to 12 carbon atoms, with at least 2 carbon atoms being situated between the nitrogen atom and the sulfur atom.

16. A process as claimed in claim 15 wherein m represents zero.

17. A process for the preparation of polyurethanes comprising reacting a compound containing isocyanate-reactive hydrogen atoms with a mixture as claimed in claim 4.

* * * * *